United States Patent [19] [11] 4,113,657
Herbstman et al. [45] Sep. 12, 1978

Best Available Copy

[54] ALKYLATION PROCESS

[75] Inventors: Sheldon Herbstman, Spring Valley; Allen N. Webb; John H. Estes, both of Wappingers Falls, all of N.Y.

[73] Assignee: Texaco Inc., New York, N.Y.

[21] Appl. No.: 746,766

[22] Filed: Dec. 2, 1976

Related U.S. Application Data

[62] Division of Ser. No. 604,586, Aug. 14, 1975, Pat. No. 4,066,716.

[51] Int. Cl.$^2$ .......... B01J 27/10
[52] U.S. Cl. .......... 252/442; 260/683.53
[58] Field of Search .......... 252/442

[56] References Cited

U.S. PATENT DOCUMENTS

| | | | |
|---|---|---|---|
| 2,924,628 | 2/1960 | Donaldson | 252/442 X |
| 3,112,351 | 11/1963 | Hoekstra | 252/442 X |
| 3,649,704 | 3/1972 | Hayes | 252/442 X |
| 3,963,643 | 6/1976 | Germanas et al. | 252/442 |

*Primary Examiner*—Patrick P. Garvin
*Attorney, Agent, or Firm*—Thomas H. Whaley; Carl G. Ries; George J. Darsa

[57] ABSTRACT

A process for the alkylation of alkanes with olefins under alkylation conditions with a catalyst having improved long term activity and composed of alumina and chlorine. The improved catalyst is prepared by contacting a catalytically active chlorided alumina composite catalyst with aluminum chloride. In a preferred embodiment the active catalyst is heat treated in an oxidizing atmosphere prior to contacting with aluminum chloride.

8 Claims, No Drawings

ALKYLATION PROCESS

This is a division of application Ser. No. 604,586 filed Aug. 14, 1975, now U.S. Pat. No. 4,066,716 issued Jan. 3, 1978.

This invention relates to the alkylation of paraffins with olefins. In particular, this invention relates to the alkylation of isoparaffins with olefins employing an improved catalyst which provides an alkylate containing high octane boiling range products.

BACKGROUND OF THE INVENTION

Chlorided alumina catalysts have been reported to be quite useful in the alkylation of paraffins with olefins, as for example the alkylation of isobutane with butene-2 or ethylene to produce high octane gasoline blending components. Typical chlorided alumina catalysts useful in alkylation are described in U.S. Pat. No. 3,240,840, 3,523,142 and 3,607,959. While the chlorided alumina alkylation catalysts described in the art possess a high degree of initial activity, this activity during alkylation is available for relatively short periods of time which detracts from the commercial attractiveness of the process. Consequently, to maintain a high degree of alkylation it is necessary to interrupt the alkylation reaction for frequent catalyst regenerations, a procedure which is costly and nonproductive in terms of reducing the amount of high octane gasoline boiling range products which would otherwise be produced.

It is therefore an object of this invention to provide a process for the alkylation of alkanes with olefins which can be undertaken for longer periods of time.

Another object of this invention is to provide an alkylation process employing a catalyst possessing improved long term activity and extended on-stream life.

Yet another object of this invention is to provide a method of improving the long term catalytic activity of a chlorided alumina catalyst and extending the on-stream time of an alkylation process.

A further object of this invention is to develope a process for the alkylation of alkanes with olefins to obtain high octane gasoline components, said process employing an improved chlorided alumina catalyst requiring less frequent regeneration.

Other objects and advantages will become apparent from a reading of the following detailed description and examples.

SUMMARY OF THE INVENTION

Broadly, this invention contemplates a process for the alkylation of alkanes with olefins which comprises contacting an alkane and an olefin under alkylation conditions with an improved catalyst comprising chlorine and alumina, said improved catalyst prepared by contacting a catalytically active chlorided alumina composite comprising from about 3.0 to 15.0 weight percent chlorine with aluminum chloride at a temperature of between 300° and 650° F. In a preferred embodiment, the catalytically active chlorided alumina composite is initially heat treated at a temperature of between 700° and 1200° F. in an oxidizing atmosphere and thereafter contacted with aluminum chloride.

In another embodiment this invention contemplates a method of improving the long term activity of an active chlorided alumina alkylation catalyst comprising from about 3.0 to 15.0 weight percent chlorine by contacting said catalyst with aluminum chloride at a temperature between 300° and 650° F. Preferably, the catalyst is initially heat treated at between 700° and 1200° F. in an oxidizing atmosphere prior to contacting with alumina chloride.

The improved chlorided alumina catalysts provided by this invention and employed in the alkylation process described herein are derived from known active chlorided alumina catalysts which consist essentially of alumina and from about 3.0 to about 15.0 weight percent chlorine. The alumina component may be any of the forms customarily employed in composite catalysts, as for example eta or gamma alumina. The active chlorided alumina catalyst is prepared by known methods, as for example contacting alumina with carbon tetrachloride, chloroform, methylene chloride, dichlorodifluoromethane, trichlorobromomethane, thionyl chloride or thiocarbonyltetrachloride under non-reducing conditions, that is, under inert or oxidizing conditions where the latter is preferred. Another method of preparing the active catalyst involves contacting alumina with a combination of chlorine and hydrogen sulfide or an organic compound such as tetrachloroethane, tetrachloroethylene, hexachloroethane, pentachloroethane, hexachloroacetone, hexachloro-1,3-butadiene, hexachloropropanone-2, hexachlorocyclopentadiene, hexachloropropylene, trichloroacryloylchloride, trichloroacetylchloride, chloral, ethane, ethylene or propane. In general, the known active chlorided alumina catalysts are prepared by contacting alumina with the activator employing temperatures of about 200° to about 800° F., most preferably between about 450° and 650° F. Further details concerning the preparation of chlorided alumina catalysts can be found in U.S. Pat. Nos. 3,240,840, 3,523,142 and 3,607,959, which are hereby incorporated by reference. In general, employing the methods of the art active alkylation catalysts are prepared consisting of alumina and from about 3.0 to about 15.0 weight percent chlorine.

The chlorided alumina catalysts prepared as described above can be provided with improved long term activity and alkylation processes employing the same with prolonged on-stream times by the procedure described above. In particular, contacting the catalyst with aluminum chloride is undertaken at a temperature of between 300° and 650° F., preferably from about 450° to 600° F. The embodiment involving an initial heat treatment of the catalytically active chlorided alumina composite in an oxidizing atmosphere is undertaken at a temperature of between 700° and 1200° F., preferably from about 850° to 1100° F.

The contacting of the active catalyst in an oxidizing atmosphere, suitably air, oxygen or mixtures containing chlorine is generally conducted at a pressure of between about 0 p.s.i.g. and 100 p.s.i.g. where the oxidizing atmosphere is preferably introduced as a flowing gaseous stream at a volumetric flow rate of at least 8 and up to about 80 standard cubic feet per hour per pound of catalyst for a period of from at least 1 hour and up to about 48 hours. It is believed that contacting of the active catalyst in the oxidizing atmosphere under the conditions described above alters and improves the catalyst's surface in a manner making it more receptive to the subsequent aluminum chloride treatment described below. The oxidizing treatment is believed to remove amounts of residue or debris associated with the catalyst's surface and derived from the initial activation treatment employing the activating compounds described above. The oxidizing treatment prepares the active catalyst's surface for further treatment according to the method of this invention by removing residue or debris and conditioning the surface of the active catalyst so as to be receptive to the further treatment with aluminum chloride.

The active catalyst, preferably following the treatment in an oxidizing atmosphere, is contacted with aluminum chloride at a temperature of between about 300° and 650° F., preferably 450° and 600° F. and under a pressure of about 0 to 300 p.s.i.g. From about 2 to 40 parts by weight of aluminum chloride per 100 parts by weight of chlorided alumina are employed in the contacting. Treatment with vaporized aluminum chloride under the conditions described above provides a further chlorination of the catalyst's surface by reacting with the residual surface hydroxyl groups bared by the cleansing action of the high temperature oxidizing treatment. This subsequent chlorination step with aluminum chloride does not, however, result in the deposition of aluminum chloride onto the catalyst's surface. Instead, the chlorided alumina composite is provided with an additional 2 to 15 weight percent chlorine. It is believed, that formation of very strong acid sites involving a complex of aluminum and chloride forms on the surface of the catalyst which provides the catalyst and alkylation process with the improved results described herein. The exact mechanism by which the complex surface is formed is not precisely understood, but it is believed to involve at least reaction with previously unreacted surface hydroxyl groups such that the catalyst's surface is essentially free of any remaining hydroxyl groups.

The improved catalyst prepared by the instant invention has been found to provide about a twofold or greater increase in long term catalyst activity as opposed to untreated active catalysts described herein or catalysts prepared by treating alumina with aluminum chloride alone. Under similar evaluation conditions wherein alkylation life measurements were made, it was found that treating activated chlorided alumina catalysts with aluminum chloride were superior to the active catalyst untreated or to a catalyst on which aluminum chloride was introduced to an alumina base.

The catalysts prepared by the instant invention can be produced in pellet, granular, bead or pulverulent form to facilitate its use in fixed beds, moving beds or fluidized solid beds as is well-known in the art. The catalyst can be activated and improved as described herein in situ in an alkylation reactor by passing the activating and improving streams so as to contact the alumina base and active catalyst under the conditions described herein.

The catalyst provided by this invention is highly active at relatively low temperatures. Alkane streams composed of n-paraffins or isoparaffins or mixtures thereof are alkylated in the presence of olefins employing the improved catalyst at temperatures within the range of about room temperature to about 500° F. and preferably within the range of about 100° to 250° F. Alkylation can be undertaken in either the liquid, vapor or liquid vapor phase. Pressures from atmospheric to the practical maximum limited by the materials of construction can be employed. Pressures ranging from about atmospheric to 1200 p.s.i.g. can also be employed. A liquid hourly space velocity, that is, the volume of liquid alkane charge per hour per volume of catalyst within the range of about 0.5 to 16, preferably within the range of about 4 to 8 is suitable for alkylation using the catalyst of this invention. Employing our catalyst a contemplated alkylation process proceeds by charging an alkane into the reaction zone together with the olefin with a mole ratio of alkane to olefin within the range of about 100:1 to 2:1, preferably 20:1 to 4:1. The on-stream time of the process may also be extended by introducing HCl along with the feed, either continuously or by means of periodic introductions. Generally, the HCl is provided in an amount of from about 2 to 2000 parts per million based on the olefin feed content.

With respect to the alkylation process, a wide range of alkanes and olefins may be employed. Generally, alkanes having from 4 to 10 carbon atoms and preferably from 4 to 8 carbon atoms are employed. Particularly preferred alkanes are the isoparaffins having 4 to 8 carbon atoms. The olefins employed during alkylation include those having from 2 to 6 carbons and preferably those having from 2 to 4 carbon atoms. Suitable alkanes used in the instant alkylation process include n-butane, n-pentane, n-hexane, n-heptane, n-octane, n-nonane, n-decane, isobutane, isopentane, isohexane and isoheptane, preferably isobutane and isopentane. Illustrative olefins include ethylene, propylene, butene-1 and -2 and amylene, preferably ethylene and propylene. Highly preferred alkylations include the reaction of ethylene with isobutane to form 2,3-dimethylbutane, the reaction of propylene and isobutane or ethylene and isopentane to form 2,2,3-trimethylbutane and the reactions of isopentylene and isobutane or isobutylene and isopentane or propylene and isohexanes to form 2,2,3,3-tetramethylpentane. Other high octane blending components which can be prepared include 2,2-dimethylpentane, 2,3-dimethylpentane, 2,2,4-trimethylpentane, 2,2,3-trimethylpentane, 2,3,4-trimethylpentane, 2,3,3-trimethylpentane and 3,3,5-trimethylheptane. The alkylate may consist of a mixture of isoparaffins of the type mentioned above, as for example from the alkylation of isobutane or isopentane with ethylene, propylene, butene and isobutylene. The alkane and olefin charge stocks may be composed of mixtures of alkanes and isoalkanes and the olefin feed stocks may be a mixture of, for example ethylene and propylene or ethylene and butene-1.

In order to more fully illustrate the nature of our invention and the manner of practicing the same, the following examples are presented.

EXAMPLE I

An active chlorided alumina catalyst was prepared by contacting 765 grams of eta alumina in a rotary reactor pressured to 30 p.s.i.g. with oxygen with 134 grams of carbon tetrachloride at 500° F. for 2 hours at autogenous pressure (about 170–250 p.s.i.g.). The resulting chlorided alumina catalyst (7% chlorine) was identified as Catalyst A.

EXAMPLE II

An active chlorided alumina catalyst was prepared by contacting 372 grams of eta alumina in a rotary reactor pressured to 30 p.s.i.g. with oxygen with 96.7 grams of aluminum chloride at 500° F. for 1 hour at autogenous pressure. The resulting catalyst contained 14% chlorine and was identified as Catalyst B.

EXAMPLE III 392 grams of Catalyst A were subsequently heated to 500° F. and contacted with 102 grams of aluminum chloride for 1 hour in a rotary reactor at 170 p.s.i.g. The resulting catalyst contained 14% chloride and was identified as Catalyst C.

EXAMPLE IV

The catalysts of Examples I, II and III were employed in the alkylation of alkanes with olefins at 80° F., 300 p.s.i.g., 0.245 WHSV of 2-butene using a 6% 2-butene in isobutane charge blend to provide an iso-$C_8$ high octane blending material. Alkylation as described above employing Catalyst C maintained a yield of at least 90% of theory for a period of time of approximately twice that of the alkylations employing Catalysts A or B.

EXAMPLE V

An active chlorided alumina catalyst is prepared by contacting 765 grams of gamma alumina in a rotary reactor pressured to 30 p.s.i.g. with oxygen and contacting with 134 grams of carbon tetrachloride at 500° F. for 2 hours. The resulting chlorided catalyst is treated with 16 liters per hour of a 9/1 volume to volume nitrogen-air mixture at 500° F. for one hour and thereafter at 16 liters per hour with the gaseous mixture at 900° F. for 3 hours. The catalyst is subsequently contacted with 193.4 grams of anhydrous aluminum chloride at 500° F. for one hour at an autogenous pressure of about 170 p.s.i.g. and the resulting catalyst contains 12–14 percent chlorine.

We claim:

1. An alkylation catalyst consisting essentially of alumina and chlorine prepared by contacting an active chlorided alumina catalyst comprising from about 3.0 to 15.0 weight percent chlorine, said alumina catalyst being prepared by contacting alumina with a chlorinating agent under non-reducing conditions, wherein said alumina catalyst is initially contacted at a temperature of between 700° and 1200° F. in an oxidizing atmosphere and thereafter with aluminum chloride at a temperature between 300° and 650° F., wherein 100 parts by weight of said alumina catalyst are contacted with from about 2 to 40 parts by weight of vaporized aluminum chloride thereby further chlorinating said alumina catalyst's surface with an additional 2 to 15 weight percent chlorine without the deposition of aluminum chloride.

2. A catalyst according to claim 1 wherein said contacting with aluminum chloride is at a temperature from about 450° to 600° F.

3. A catalyst according to claim 1 wherein said contacting in an oxidizing atmosphere is at a temperature from about 850° to 1100° F.

4. A catalyst according to claim 1 wherein said oxidizing atmosphere flows through said catalyst at a volumetric flow rate of at least 8 and up to about 80 standard cubic feet per hour per pound of catalyst for at least one and up to 48 hours.

5. A method of improving the long term activity of an active chlorided alumina alkylation catalyst consisting essentially of from about 3.0 to 15.0 weight percent chlorine and alumina, said alumina catalyst being prepared by contacting alumina with a chlorinating agent under non-reducing conditions, wherein said alumina catalyst is initially contacted at a temperature of between 700° and 1200° F. in an oxidizing atmosphere and thereafter with aluminum chloride at a temperature between 300° and 650° F., wherein 100 parts by weight of said alumina catalyst are contacted with from 2 to 40 parts by weight of vaporized aluminum chloride thereby further chlorinating said alumina catalyst's surface with an additional 2 to 15 weight percent chlorine without the deposition of aluminum chloride.

6. A method according to claim 5 wherein said contacting with aluminum chloride is at a temperature from about 450° to 600° F.

7. A method according to claim 5 wherein said contacting in an oxidizing atmosphere is at a temperature from about 850° to 1100° F.

8. A method according to claim 5 wherein said oxidizing atmosphere flows through said catalyst at a volumetric flow rate of at least 8 and up to about 80 standard cubic feet per hour per pound of catalyst for at least one and up to 48 hours.

* * * * *